United States Patent
Shi (10) Patent No.: US 12,414,799 B2
(45) Date of Patent: Sep. 16, 2025

(54) MEDICAL DEVICE HAVING VISUAL PUNCTURE APPARATUS

(71) Applicant: Jun Shi, Shanghai (CN)

(72) Inventor: Jun Shi, Shanghai (CN)

(73) Assignee: Jun Shi, Shanghai (CN)

( * ) Notice: Subject to any disclaimer, the term of this patent is extended or adjusted under 35 U.S.C. 154(b) by 626 days.

(21) Appl. No.: 16/824,141

(22) Filed: Mar. 19, 2020

(65) Prior Publication Data

US 2020/0214739 A1    Jul. 9, 2020

Related U.S. Application Data

(63) Continuation of application No. PCT/CN2018/087819, filed on May 22, 2018.

(30) Foreign Application Priority Data

Sep. 20, 2017    (CN) .......................... 201710853548.4

(51) Int. Cl.
  *A61B 17/34*    (2006.01)
  *A61B 1/00*    (2006.01)
  (Continued)

(52) U.S. Cl.
  CPC ........ *A61B 17/3478* (2013.01); *A61B 1/0008* (2013.01); *A61B 1/00158* (2013.01);
  (Continued)

(58) Field of Classification Search
  CPC .............. A61B 17/3403; A61B 90/361; A61B 1/00158; A61B 1/05; A61B 1/0661;
  (Continued)

(56) References Cited

U.S. PATENT DOCUMENTS

| 6,235,015 | B1 * | 5/2001 | Mead, III ............. A61B 18/203 606/9 |
| 6,419,654 | B1 * | 7/2002 | Kadan .................. A61M 1/774 600/101 |

(Continued)

FOREIGN PATENT DOCUMENTS

| CN | 204318870 U | 5/2015 |
| CN | 106963459 A | 7/2017 |

(Continued)

OTHER PUBLICATIONS

International Search Report (in English and Chinese) and Written Opinion issued in PCT/CN2018/087819, mailed Jun. 27, 2018, 10 pages provided.

(Continued)

*Primary Examiner* — Ryan N Henderson
*Assistant Examiner* — Pamela F Wu
(74) *Attorney, Agent, or Firm* — HSML P. C.

(57) ABSTRACT

This application provides a medical device having a visual puncture apparatus. The visual puncture apparatus comprises a puncture needle, an ultrasound probe, an imaging assembly, and a display device, wherein a distal end of the puncture needle has a puncture tip and is provided with a working channel therein, the imaging assembly is used for image processing and a part thereof is arranged in the working channel, and the display device is used to display images from the imaging assembly and images from the ultrasound probe. The medical device having a visual puncture apparatus of the present application can puncture to a lesion under direct vision, and the entire puncture process is visible. The details of the puncture path are intuitively reflected on the monitor like a camera, which is intuitive and real-time. The safety and accuracy of the conventional interventional puncture process is improved.

12 Claims, 6 Drawing Sheets

(51) Int. Cl.
*A61B 1/05* (2006.01)
*A61B 1/06* (2006.01)
*A61B 1/07* (2006.01)
*A61B 90/00* (2016.01)

(52) U.S. Cl.
CPC .............. *A61B 1/05* (2013.01); *A61B 1/0661* (2013.01); *A61B 1/07* (2013.01); *A61B 17/3403* (2013.01); *A61B 17/3421* (2013.01); *A61B 90/361* (2016.02); *A61B 2017/3413* (2013.01); *A61B 2090/378* (2016.02)

(58) Field of Classification Search
CPC . A61B 1/07; A61B 17/3421; A61B 2090/378; A61B 17/3478; A61B 17/3474; A61B 17/3476; A61B 17/3417; A61B 1/0669; A61B 1/06; A61B 1/00066; A61B 1/00105; A61B 1/00154; A61B 1/00135; A61B 1/00101; A61B 17/3426; A61B 2017/3425–3429; A61B 2017/3445; A61B 2017/320074; A61B 17/34; A61B 2090/3614; A61B 1/0008; A61B 1/00131–00133; A61B 1/012; A61B 1/018
USPC .......................................................... 606/185
See application file for complete search history.

(56) References Cited

U.S. PATENT DOCUMENTS

| | | | | |
|---|---|---|---|---|
| 10,092,176 | B2* | 10/2018 | Kienzle | A61B 1/0676 |
| 10,368,885 | B2* | 8/2019 | Wan | A61B 17/221 |
| 2005/0077689 | A1* | 4/2005 | Hueil | A61B 17/3421 |
| | | | | 277/628 |
| 2008/0243162 | A1* | 10/2008 | Shibata | A61B 17/3417 |
| | | | | 606/185 |
| 2013/0296691 | A1* | 11/2013 | Ashe | A61B 5/6848 |
| | | | | 600/424 |
| 2014/0249371 | A1* | 9/2014 | Fischvogt | A61B 1/00131 |
| | | | | 600/114 |
| 2015/0025311 | A1* | 1/2015 | Kadan | A61B 17/3474 |
| | | | | 600/104 |
| 2015/0313634 | A1 | 11/2015 | Gross et al. | |
| 2016/0015423 | A1* | 1/2016 | Ravikumar | A61B 17/29 |
| | | | | 604/164.11 |
| 2016/0067391 | A1* | 3/2016 | Real | A61B 17/3421 |
| | | | | 604/543 |
| 2016/0278694 | A1 | 9/2016 | Aharoni et al. | |
| 2016/0296108 | A1 | 10/2016 | Kienzle | |
| 2016/0331343 | A1 | 11/2016 | Hunter et al. | |
| 2017/0055813 | A1* | 3/2017 | London Brown | A61B 1/00154 |
| 2017/0265879 | A1* | 9/2017 | Washburn, II | A61B 1/317 |

FOREIGN PATENT DOCUMENTS

| | | |
|---|---|---|
| CN | 107019547 A | 8/2017 |
| CN | 206434352 U | 8/2017 |
| JP | 4533615 B2 | 9/2010 |

OTHER PUBLICATIONS

Notice of Reasons for Refusal issued in Japanese Application No. 2020-537821, mailed Mar. 23, 2021, with English machine translation.

Communication issued in European Application No. 18859903.9, dated Jun. 23, 2023.

* cited by examiner

MEDICAL DEVICE HAVING VISUAL PUNCTURE APPARATUS

CROSS REFERENCE TO RELATED APPLICATIONS

This application claims the priority of Chinese patent application No. 2017108535484, entitled "Medical device having visual puncture apparatus" filed on Sep. 2, 2017; the entire disclosure thereof is incorporated herein by reference.

TECHNICAL FIELD

The invention relates to a medical device, in particular to a medical device having a puncture function.

TECHNICAL BACKGROUND

At present, in the minimal invasive surgery, the basic surgical procedure is as follows: firstly, a puncture is performed through a puncture needle; after the puncture is completed, the puncture needle is removed and the wound is enlarged with a reaming cannula; and then instrument(s) is/are inserted along the reaming cannula to perform procedures such as tissue removal and other surgeries. In the above process, when a puncture is performed with a puncture needle, it is usually performed with the assistance of an ultrasound probe. However, due to the characteristics of ultrasound technology, it is difficult for the operator to puncture the target position accurately at one time. As a result, multiple punctures may be required, resulting in increased trauma, delayed recovery, and possibly infection.

In addition, traditional puncture can not directly observe the puncture path, which often causes damage to tissue or blood vessel, which brings pain to patients.

Therefore, there is a need for a minimal invasive surgical instrument with more accurate positioning, simpler operation, and smaller wounds.

SUMMARY

This invention aims to provide a medical device having a visual puncture apparatus, which can achieve both puncture and other diagnostic and therapeutic functions.

In order to achieve the above aims, the present invention provides a medical device having a visual puncture apparatus, the visual puncture apparatus comprises a puncture needle, an imaging assembly, and a display device, wherein a distal end of the puncture needle has a puncture tip and is provided with a working channel therein, the imaging assembly is configured to be capable of image acquiring, transmitting and processing, at least a portion of the imaging assembly is arranged in the working channel, and the display device is configured to display images from the imaging assembly.

In one preferred embodiment, the working channel is a single channel without any internal partition.

In one preferred embodiment, the working channel is provided to be suitable for arranging at least a part of the imaging assembly and an additional instrument at the same time therein; or the working channel is provided to be suitable for arranging at least a part of the imaging assembly therein, meanwhile to be capable of performing perfusion administration, suction or cleaning via the working channel.

In one preferred embodiment, the working channel is configured to be suitable for simultaneously arranging at least a part of the imaging assembly and an additional instrument and tool therein, wherein the instrument and tool are one or more selected from the following: a laser, a radio frequency device, a microwave device, an ultrasonic lithotripsy system, a pneumatic ballistic lithotripsy system, a vibration device, a drill, a guide wire, a radiofrequency ablation device, a sample collecting device, and an irrigation device.

In one preferred embodiment, the puncture needle is detachably connected to the imaging assembly.

In one preferred embodiment, the visual puncture apparatus further comprises a coupler, and the puncture needle is detachably connected to the imaging assembly through the coupler.

In one preferred embodiment, the visual puncture apparatus further comprises a multi-port connecter, wherein the multi-port connecter is disposed at a proximal end of the puncture needle and is communicated with the puncture needle.

In one preferred embodiment, the visual puncture apparatus further comprises a light source, and the imaging assembly of the medical device comprises imaging and illumination fibers, wherein the imaging and illumination fibers extend through the puncture needle or the puncture cannula and is connected to the light source.

In one preferred embodiment, the outer surface of the imaging and illumination fiber is processed so that it is capable of experiencing sterilization operations without affecting reuse.

In one preferred embodiment, the visual puncture apparatus further comprises a shifter configured to be capable of adjusting the relative position between the imaging and illumination fibers and the puncture needle.

In one preferred embodiment, the distal end of the imaging and illumination fiber is covered with a transparent protective cover.

In one preferred embodiment, a lens assembly is provided at a distal end of the imaging and illumination fiber.

In one preferred embodiment, a distal end of the imaging and illumination fiber is provided with a lens made of a gemstone having a Mohs hardness higher than 7.5.

In one preferred embodiment, the lens is a fish-eye lens.

In one preferred embodiment, the visual puncture apparatus further comprises an ocular, the ocular being connected to the imaging assembly to receive image information from the imaging assembly.

In one preferred embodiment, the imaging assembly further comprises a lens assembly, the lens assembly being located inside a distal end of the puncture needle; alternatively, the imaging assembly comprises a signal transmitting cable and an image sensor, wherein the image sensor is disposed at the distal end of the puncture needle, and is electrically connected to the display device via the signal transmitting cable extending through the interior of the puncture needle.

In one preferred embodiment, the outer diameter of the puncture needle is 0.35 mm to 3.2 mm. For example, the outer diameter of the puncture needle is 0.35 mm, or 0.4 mm, or 0.45 mm, or 0.6 mm, or 0.9 mm, or 1.32 mm, or 1.53 mm, or 2.07 mm, or 2.55 mm.

In one preferred embodiment, the medical device is suitable for the following diseases: lithiasises, cysts, tumors, neurological diseases, facet joint diseases, spinal diseases, precision localized cell therapy, orthopedic treatments, nerve damage treatment and targeted anesthesia.

In one preferred embodiment, the visual puncture apparatus further comprises an ultrasound probe, and the display device is further configured to display the image from the ultrasound probe.

In one preferred embodiment, the visual puncture apparatus further comprises a positioner arranged such that it can be detected by the ultrasound probe and the relevant image can be shown on the display device.

In one preferred embodiment, the positioner is a magnetic sensor.

This invention also provides a medical device having a visual puncture apparatus, wherein the visual puncture apparatus comprises a puncture assembly, an imaging assembly, and a display device, wherein the puncture assembly comprises a puncture needle and a puncture cannula, wherein the puncture cannula is detachably sleeved around the puncture needle, the distal end of the puncture needle has a puncture tip, the puncture assembly has a working channel therein, and the imaging assembly is configured to enable image acquiring, transmitting and processing, at least a part of the imaging assembly is arranged in the working channel, and the display device is used to display an image from the imaging assembly.

In one preferred embodiment, the working channel is disposed in the puncture needle and/or the puncture cannula, and the working channel is a single channel without any internal partition.

In one preferred embodiment, the working channel is provided to be suitable for arranging at least a part of the imaging assembly and an additional instrument at the same time therein; or the working channel is provided to be suitable for arranging at least a part of the imaging assembly therein, meanwhile to be capable of performing perfusion administration, suction or cleaning via the working channel.

In one preferred embodiment, the working channel is configured to be suitable for simultaneously arranging at least a part of the imaging assembly and an additional instrument and tool therein, wherein the instrument and tool are one or more selected from the following: a laser, a radio frequency device, a microwave device, an ultrasonic lithotripsy system, a pneumatic ballistic lithotripsy system, a vibration device, a drill, a guide wire, a radiofrequency ablation device, a sample collecting device, and an irrigation device.

In one preferred embodiment, the puncture needle is detachably connected to the imaging assembly.

In one preferred embodiment, the visual puncture apparatus further comprises a multi-port connecter, wherein the multi-port connecter is disposed at a proximal end of the puncture needle and is communicated with the puncture needle.

In one preferred embodiment, the visual puncture apparatus further comprises a light source, and the imaging assembly of the medical device comprises imaging and illumination fibers, wherein the imaging and illumination fibers extend through the puncture needle or the puncture cannula and is connected to the light source.

In one preferred embodiment, the outer surface of the imaging and illumination fiber is processed so that it is capable of experiencing sterilization operations without affecting reuse.

In one preferred embodiment, the visual puncture apparatus further comprises a shifter configured to be capable of adjusting the relative position between the imaging and illumination fibers and the puncture needle or the puncture cannula.

In one preferred embodiment, the distal end of the imaging and illumination fiber is covered with a transparent protective cover.

In one preferred embodiment, a lens assembly is provided at a distal end of the imaging and illumination fiber.

In one preferred embodiment, a distal end of the imaging and illumination fiber is provided with a lens made of a gemstone having a Mohs hardness higher than 7.5.

In one preferred embodiment, the lens is a fish-eye lens.

In one preferred embodiment, the visual puncture apparatus further comprises an ocular, the ocular being connected to the imaging assembly to receive image information from the imaging assembly.

In one preferred embodiment, the imaging assembly further comprises a lens assembly, the lens assembly being located inside a distal end of the puncture needle; alternatively, the imaging assembly comprises a signal transmitting cable and an image sensor, wherein the image sensor is disposed at the distal end of the puncture needle or puncture cannula, and is electrically connected to the display device via the signal transmitting cable extending through the puncture needle or the interior of the puncture cannula.

In one preferred embodiment, the outer diameter of the puncture cannula or the puncture needle is 0.35 mm-3.2 mm. For example, the outer diameter of the puncture cannula or the puncture needle is 0.35 mm, or 0.4 mm, or 0.45 mm, or 0.6 mm, or 0.9 mm, or 1.32 mm, or 1.53 mm, or 2.07 mm, or 2.55 mm.

In one preferred embodiment, the medical device is suitable for the following diseases: lithiasises, cysts, tumors, neurological diseases, facet joint diseases, spinal diseases, precision localized cell therapy, orthopedic treatments, nerve damage treatment and targeted anesthesia.

In one preferred embodiment, the visual puncture apparatus further comprises an ultrasound probe, and the display device is further configured to display the image from the ultrasound probe.

In one preferred embodiment, the visual puncture apparatus further comprises a positioner arranged such that it can be detected by the ultrasound probe and the relevant image can be shown on the display device.

In one preferred embodiment, the positioner is a magnetic sensor.

This invention also provides a medical device having a visual puncture apparatus, the visual puncture apparatus comprises a puncture assembly, an imaging assembly, and a display device, wherein the interior of the puncture assembly has a working channel therein and comprises a puncture needle, and the distal end of the puncture needle has a puncture tip, and the imaging assembly comprises a signal acquiring element and a signal transmitting cable, wherein the signal acquiring element is disposed at the distal end of the puncture assembly and is electrically connected to the display device via the signal transmitting cable extending through the working channel, and the display device is used to display images from the imaging assembly.

In one preferred embodiment, the working channel is configured to simultaneously arrange with at least a part of the imaging assembly and an additional instrument inside the working channel.

In one preferred embodiment, the additional instrument is selected from one or more of the following tools: laser, radio frequency device, microwave device, ultrasonic lithotripsy system, pneumatic ballistic lithotripsy system, vibration device, drill, guide wire, radiofrequency ablation device, sample collection device and irrigation devices, etc.

In one preferred embodiment, the visual puncture apparatus further comprises a multi-port connecter, wherein the multi-port connecter is disposed at a proximal end of the puncture assembly and is communicated with the puncture assembly.

In one preferred embodiment, the signal acquiring element is a CCD sensor or a CMOS sensor.

In one preferred embodiment, the visual puncture apparatus further comprises a puncture sleeve, the puncture sleeve is detachably sleeved around the periphery of the puncture needle.

In one preferred embodiment, the outer diameter of the puncture needle or the puncture cannula is 0.35 mm to 3.2 mm.

In one preferred embodiment, the working channel is provided inside the puncture needle, or inside the puncture cannula, or between the puncture needle and the puncture cannula.

In one preferred embodiment, the medical device is suitable for the following diseases or treatment methods: lithiasises, cysts, tumors, neurological diseases, facet joint diseases, spinal diseases, precision localized cell therapy, orthopedic treatments, nerve damage treatment and targeted anesthesia.

In one preferred embodiment, the visual puncture apparatus further comprises an ultrasound probe, and the display device is further configured to display the image from the ultrasound probe.

In one preferred embodiment, the visual puncture apparatus further comprises a positioner arranged such that it can be detected by the ultrasound probe and the relevant image can be shown on the display device.

In one preferred embodiment, the positioner is a magnetic sensor.

The medical device having a visual puncture apparatus of the present application can perform visual puncture operation very intuitively and accurately because the puncture needle is provided with an imaging assembly such as a camera element therein and combined with ultrasound guidance, and after the puncture, the diagnosis and treatment operation can be directly performed, and the wound caused by the operation is small.

EMBODIMENTS

The preferred embodiment of this invention will be described in detail with reference to the accompanying drawings, so that the purposes, the characteristics and the advantages of the invention can be more clearly understood. It should be understood that the embodiments shown in the figures are not intended to limit the scope of this invention, but illustrate the essential spirit of the technical solution of this invention.

In the following description, certain specific details are set forth for the purpose of illustrating various disclosed embodiments to provide a thorough understanding of the various embodiments. One skilled in the art will recognize, however, that the embodiments may be realized without one or more of these specific details. In other cases, well-known devices, structures, and techniques associated with the present application may not be shown or described in detail to avoid unnecessarily obscuring the description of the embodiments.

The words "including" and variations such as "comprising" and "having" in the specification and claims should be construed as open and inclusive meaning that they should be construed as "including, but not limited to", unless the context requires otherwise.

Reference throughout the specification to "one embodiment" or "an embodiment" means that a particular feature, structure, or characteristic described in connection with the embodiment is included in at least one embodiment. Thus, expression of "in one embodiment" or "In one embodiment" in various places throughout the specification are not necessarily all referring to the same embodiment. Furthermore, the particular features, structures, or characteristics may be combined in any manner in one or more embodiments.

As used in this specification and the appended claims, the singular forms "a", "the" and "said" include plural referents unless the context clearly dictates otherwise. It should be noted that the term "or" is generally used in its sense including "and/or" unless the context clearly dictates otherwise.

In the following description, in order to clearly show the structure and working mode of the present invention, many words about direction will be used to describe it. Words such as "front", "rear", "left", "right", "outside", "inside", "outward", "inward", "up", "down" should be deemed as words for convenience and should not be deems as word for limiting.

Figure 1:
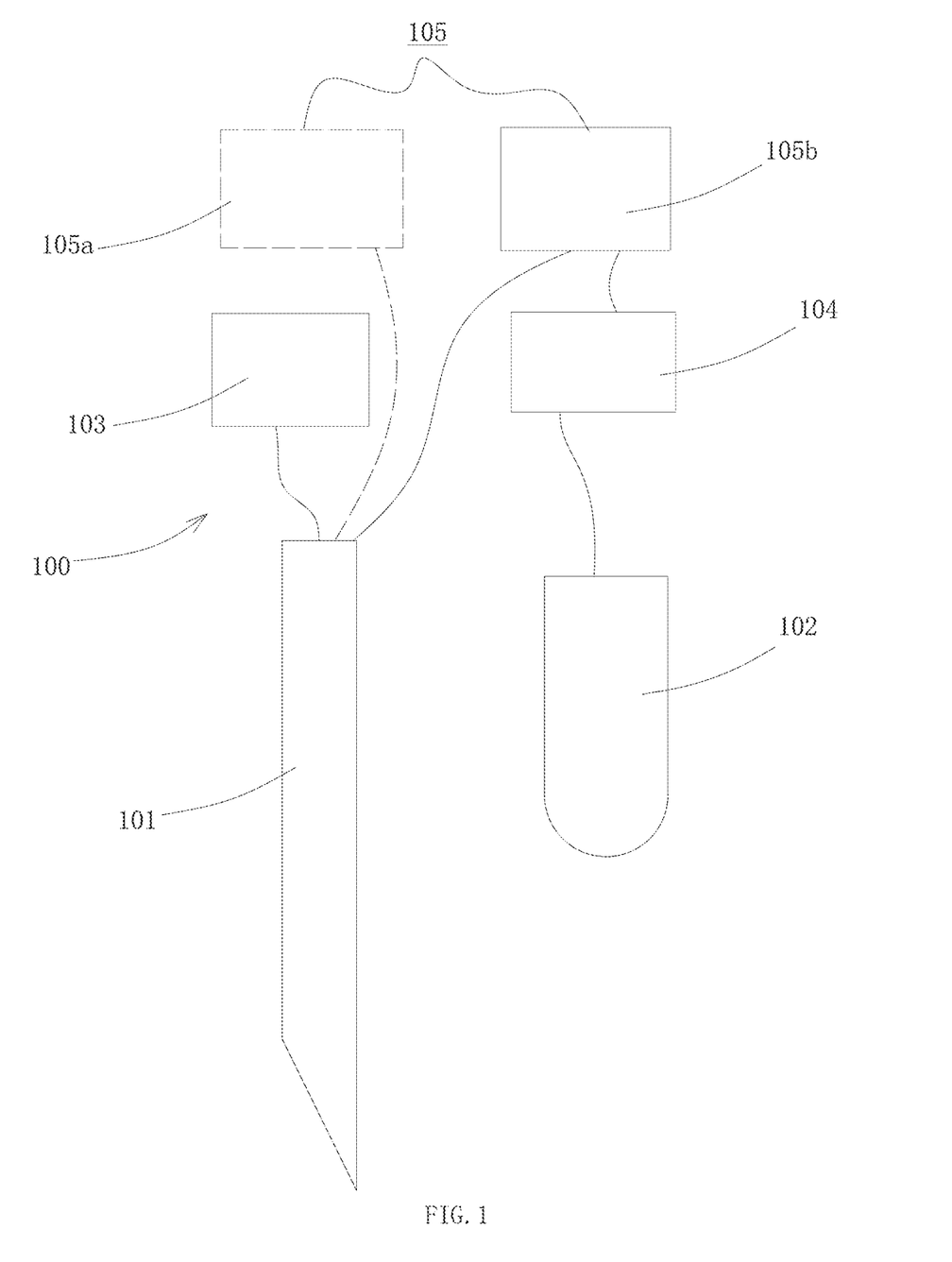
FIG. 1 is a system diagram of a medical device having a visual puncture apparatus according to the present invention.

FIG. 1 is a system diagram of a medical device 100 with a visual puncture apparatus according to an embodiment of the present invention. As shown in FIG. 1, the medical device 100 comprises a puncture needle 101, an ultrasound probe 102, a light source 103, an ultrasound host 104, and a monitor 105. At least a part of an imaging assembly (not shown in FIG. 1) is installed in the puncture needle 101. The imaging assembly is connected to the monitor 105 via a cable, so that an image from the imaging assembly can be displayed on the monitor 105. The imaging assembly is used for image acquiring, transmitting and processing. In this embodiment, the imaging assembly comprises an optical device and an image processing device, wherein the optical device is used for image acquiring and image information transmitting, and the image processing device can process the image information from the optical device and convert it into electrical signals displayed on the monitor 105. The optical device comprises an imaging and illumination fiber 9 (see FIG. 3), a lens assembly, an ocular, and the like. The distal end of the imaging and illumination fiber 9 may be covered with a transparent protective cover. The transparent protective cover can be used as a lens assembly at the same time. Preferably, the distal end of the imaging and illumination fiber 9 is provided with a lens made of gemstones.

Preferably, the lens is a fish-eye lens, also known as a wide-angle lens. Preferably, the fisheye lens is made of a gemstone having a Mohs hardness greater than 7.5. The light source 103 provides light for the imaging and illumination fiber 9. It should be understood that the imaging assembly may also adopt other types of devices, such as an image sensor (CCD sensor, CMOS sensor, etc.) or other signal acquiring element applied to video technology, which is communicated to the monitor through a signal transmitting cable.

The ultrasound probe 102 is connected to an ultrasound host 104. The image information obtained by the ultrasound probe 102 is processed by the ultrasound host 104 and transmitted to the monitor 105 to display an image. Here, the ultrasound probe and the ultrasound host can be any suitable ultrasound diagnostic apparatus known in the art or to be developed, such as GE's GE LOGIQ E9 ultrasound diagnostic apparatus.

The monitor 105 may comprise a monitor 105a and a monitor 105b. Image information from the imaging assembly and the ultrasound probe can be displayed on the monitor 105a and the monitor 105b, respectively. It should be understood that the monitor 105 may comprise only the monitor 105a (or monitor 105b), and the image information from both the imaging assembly and the ultrasound probe are displayed on the monitor 105a (or monitor 105b).

Figure 2:
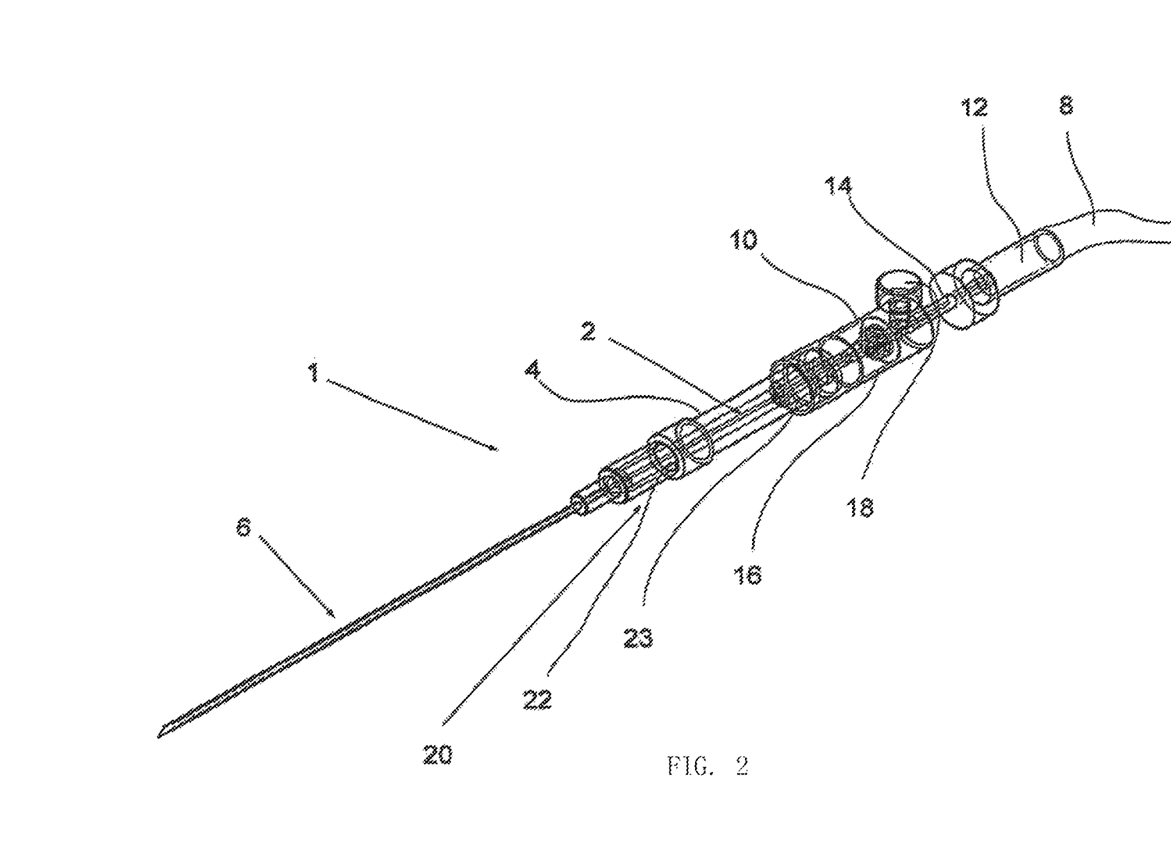
FIG. 2 is a perspective view of a part of a visual puncture apparatus according to an embodiment of the present invention.

FIG. 2 shows a schematic perspective view of a module 1 consisting of a part of an imaging assembly and a puncture needle of a visual puncture apparatus. The module 1 mainly consists of an optical device 2. The optical device 2 is connected to the puncture needle 6 through a connecter 4. The optical device 2 contains an imaging and illumination fiber bundle, at least a part of which is housed in a puncture needle 6. The optical device illuminates an inspected area, and an image information is sent to an ocular or a connected image processing device. The image processing device is used to process the image information and convert it into an electric signal suitable for display on a monitor. The optical device 2 may be designed to have a resolution between 3,000 and 50,000 pixels, or higher for the intended use. In FIG. 2, a protection tube 8 is provided at the rear of the optical device 2, and the protection tube 8 protects the portion from external influences. The rear of the optical device 2 extends away from the connection 4 and faces an ocular which is suitable for separation and which can be designed, for example, as a zoom ocular. Of course, the ocular can also be a non-zoom ocular. A distal end portion of the optical device 2 facing the area to be observed is provided with a lens assembly.

Figure 6:
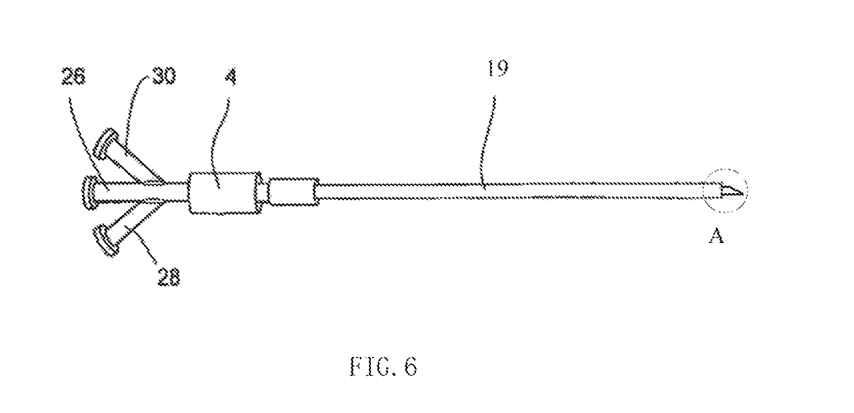
FIG. 6 is a perspective view of a part of a visual puncture apparatus according to another embodiment of the present invention.
Figure 6A:
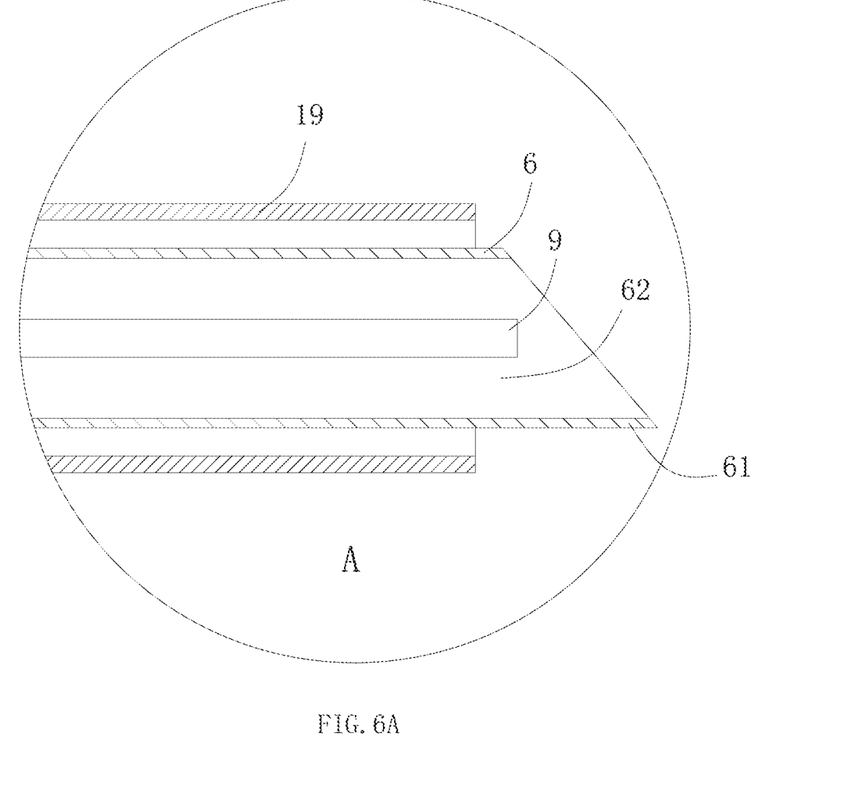
FIG. 6A is the enlarged cross-sectional view of the detail A in FIG. 6.

The distal end of the puncture needle has a puncture tip 61 and is provided with a working channel 62 (also referred to as a first working channel 62) inside, see FIG. 6A. Preferably, the working channel 62 is a single channel without any internal partition. The working channel 62 is provided so as to be suitable for arranging a part of the above-mentioned imaging assembly inside. In one embodiment, after accommodating a part of the imaging assembly, there is still a space in the working channel for medicines, cleaning liquids, etc. to enter for cleaning or administration. Preferably, the working channel 62 can also be equipped with additional instruments. The additional instruments are selected from one or more of the following tools: laser, radio frequency device, microwave device, ultrasonic lithotripsy system, pneumatic ballistic lithotripsy system, vibration device, drill, guide wire, radiofrequency ablation device, sample collection device and irrigation devices, etc., to achieve different therapeutic purposes. The diameter of the puncture needle 6 is set to be suitable for the corresponding application. Preferably, the outer diameter of the puncture needle ranges from 0.35 mm to 3.2 mm. More preferably, the outer diameter of the puncture needle ranges from 0.9 mm to 2.5 mm. For example, the outer diameter of the puncture needle is 0.35 mm, or 0.4 mm, or 0.45 mm, or 0.6 mm, or 0.9 mm, or 1.32 mm, or 1.53 mm, or 2.07 mm, or 2.55 mm. The puncture needle 6 is made of stainless steel or other hard materials. The puncture needle 6 can be selected according to the intended purpose.

Figure 4:
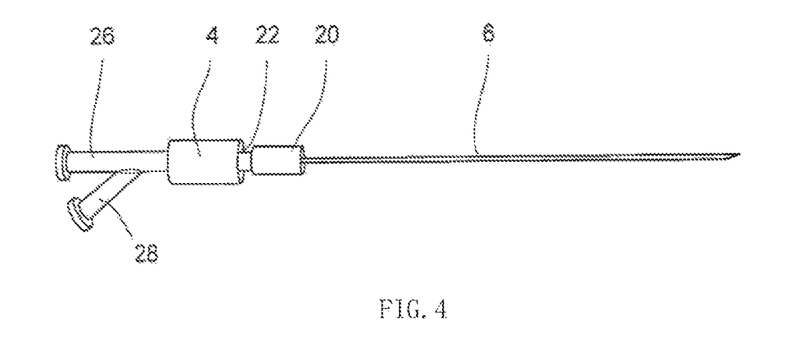
FIG. 4 shows a perspective view of a variant of FIG. 3.
Figure 5:
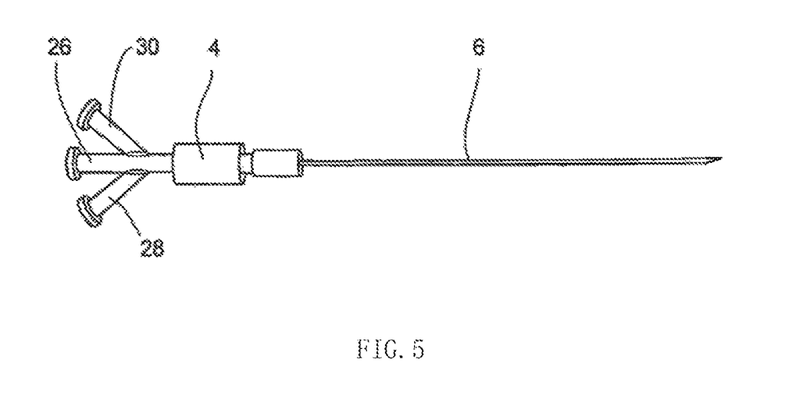
FIG. 5 shows a perspective view of another variant of FIG. 3.

With continued reference to FIG. 2, the optical device 2 and the puncture needle 6 are connected by a connecter 4. In the embodiment shown in FIG. 2, the connecter 4 is designed as a single-port connecter. It should be understood that the connecter 4 may also be a multi-port connecter having more ports (as shown in FIGS. 4 and 5). The connecter 4 is made of plastic. For different diagnostic and therapeutic purposes, multiple different puncture needles 6 and connecters 4 are assigned to a single optical device 2. The basic adjustment of the length of the optical device and the length of the catheter is achieved by a suitable lateral cutting of the protection tube 8, so it is easy to implement even for a layman. Then, precise length adjustment is achieved by an adjustment device referred to as a shifter 10 hereinafter. The shifter 10 is connected to the optical device 2 via a connecter, and more specifically to the protection tube 8. The shifter 10 comprises a guide catheter surrounding the optical device 2. A slider 16 connected to the puncture needle 6 is movably guided along the guide catheter. The shifter 10 is adapted to be fixed on the guide catheter 14 by a locking screw 18, so that the optical fiber of the optical device 2 is adapted to move correspondingly in the puncture needle 6 until the distal end of the optical device 2 is located in the right place in the puncture needle near the puncture tip. The locking screw 18 is then tightened to fix their relative positions. In the illustrated embodiment, the puncture needle 6 is detachably connected to the puncture needle connection portion 22 via a coupler 20. The connecter 4 is detachably connected to the shifter 10 through a suitable coupling member 23. The couplers 20 and 23 can be, for example, Luer couplers.

Figure 3:
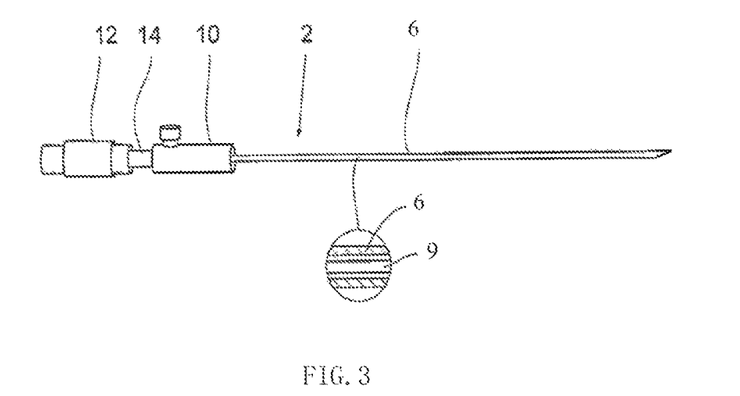
FIG. 3 is a perspective view of a portion of FIG. 2 of the present invention.

As already mentioned, the diameter, length and material of the puncture needle 6 can be selected according to the intended purpose. As will be explained in more detail below, both the puncture needle 6 and the connecter 4 can be designed as disposable members, delivered in aseptic packaging, and discarded after a single use. Therefore, only the optical device 2 must be decontaminated. The outer surface of the imaging and illumination fiber of the optical device 2 is processed so that it is capable of experiencing sterilization operations without affecting reuse. For example, the outer surface of the imaging and illumination fiber may be coated with a coating of a specific material. The specific material may be a material such as Teflon. Alternatively, the outer surface of the imaging and illumination fiber can be wrapped with a layer of abrasion-resistant and heat-resistant film. FIG. 3 shows a partial view of the optical device 2 of FIG. 2. The bending protective connection portion 12, the guide catheter 14, the shifter 10, and the protruding distal portion of the optical device 2 are housed in the puncture needle 6 and the connecter 4 in FIG. 1.

In this embodiment, a protection tube (not shown) may be further provided to protect the sensitive image light conductor and the lens assembly, thereby preventing damage. The protection tube is kept over the fiber during storage, transportation, and decontamination.

In order to connect the puncture needle 6 to the sterilized optical device 2, the distal end portion of the optical device 2 is inserted into the puncture needle 6. FIG. 4 shows an embodiment of a puncture needle 6 attached to a puncture needle connection portion 22 of a connecter 4 via a Luer coupler 20, wherein the connecter 4 is provided with an axial connection portion or outlet 26 and an inclined connection portion 28. The portion of the coupler 20 (Luer lock) near puncture needle is made of steel. The optical device 2 is preferably inserted into the axial connection portion 26 and then into the puncture needle 6, while the connection portion 28 is used to connect the irrigation tube.

FIG. 5 shows a variant of FIG. 3, in which the connecter 4 is designed with three connecting portions: the axial connecting portion 26, the inclined connection portion 28, and another inclined connection portion 30 disposed symmetrically with the inclined connection portion 28. In this variant, the optical device 2 is inserted into one of the inclined connection portions 28 and 30. For example, it may be connected to a tool, such as a biopsy forceps, a small basket for lithiasis removal, or a micro drill, through the central axial connection portion 26. The irrigation tube can be connected to the inclined connection portions 28 and 30 remained again.

FIG. 6-6A illustrate a perspective view of a portion of a visual puncture apparatus according to another embodiment of the present invention. As shown in FIGS. 6-6A, a puncture cannula 19 is surrounded over the outside of the puncture needle 6. The puncture needle 6 and the puncture cannula 19 together form a puncture assembly. The puncture cannula 19 is detachably sleeved around the puncture needle. The puncture tip of the puncture needle 6 is located at the front end of the puncture assembly and protrudes from the puncture cannula 19. The puncture assembly has a working channel (also referred to as a second working channel) inside. The second working channel may be a single channel without any internal separation. The second working channel can be arranged in the puncture cannula 19 and/or in the puncture needle 6. At least part of the above-mentioned imaging assembly and at least part of the medical instrument may be arranged in the second working channel. The additional instruments can be one or more selected from the following tools: laser, radio frequency device, microwave device, ultrasonic lithotripsy system, pneumatic ballistic lithotripsy system, vibration device, drill, guide wire, radiofrequency ablation device, sample collection device and irrigation devices, etc. In this embodiment, the structure of the puncture needle 6 may be the same as that of the above-mentioned embodiment, or may be different from that of the above-mentioned embodiment. For example, the puncture needle 6 may be solid, and at this time, at least part of the imaging assembly can be arranged in the puncture cannula 19. Both the puncture needle 6 and the puncture cannula 19 can be designed as disposable members, delivered in aseptic packaging, and discarded after a single use.

Both the puncture cannula 19 and the puncture needle 6 are connected to the connecter 4. The connecter 4 has three outlets or connection portions 26, 28, and 30, which can be entered for different instruments, respectively. After puncturing is completed, the puncture needle 6 and the optical fiber can be separated from the puncture cannula 19, and only the puncture cannula 19 is left at the surgical site. Other instruments can enter the human body through the puncture cannula for diagnosis or treatment. Since the puncture cannula 19 has a larger diameter than the diameter of the puncture needle, it can accommodate larger instruments, so that more instruments or larger instruments can enter the human body through the puncture cannula for treatment.

Figure 7:
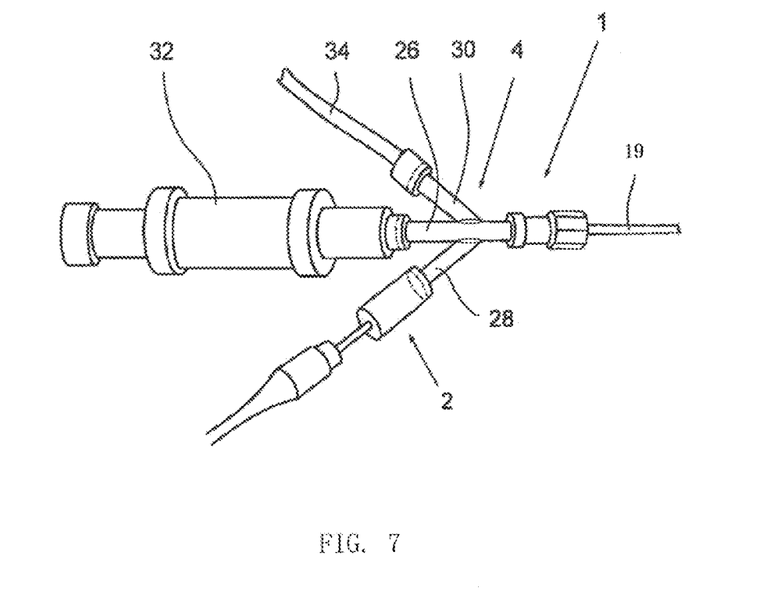
FIG. 7 shows an example of an endoscope equipped with an instrument tool designed according to FIG. 5.

FIG. 7 shows a partial view of the endoscope 1 adopting the structure of the present invention. This endoscope 1 contains the optical device of FIG. 2, the puncture cannula 19 of FIG. 6, and the connecter 4. The optical device 2 is connected to the inclined connection portion 28. In the above-mentioned endoscope, it is required that the optical device 2 (for example, an optical fiber) is designed to be semi-rigid or flexible so as to insert the puncture cannula 19 through the inclined connection portion 28 without damage. For this purpose, the connecter 4 has a smooth surface in the area between the inclined connection portion and the subsequent axial area, so that it is suitable for the optical device 2 to be slidably inserted. In this embodiment, a drilling tool 32 is connected to the central axial outlet 26. An irrigation tube 34 is connected to another inclined connection portion 30. Of course, if entering through the straight connection portion 26, the optical device 2 not only can be designed as semi-rigid or flexible element, but also can be designed as rigid element.

Figure 8:
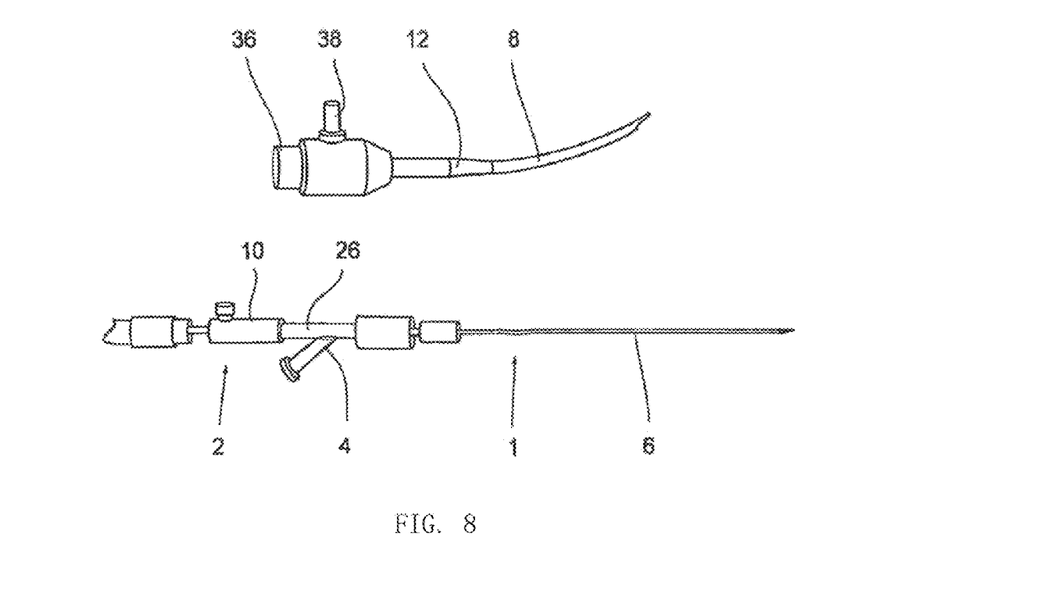
FIG. 8 shows a partial view of the diagnostic endoscope 1 with the puncture needle 6 and the connecter 4 of FIG. 4.

FIG. 8 shows a partial view of the endoscope 1 with the puncture needle 6 and the connecter 4 of FIG. 4. The optical device 2 is inserted into the axial outlet 26 and is aligned with the aperture of the puncture needle 6 by the shifter 10. The area of the optical device 2 behind the shifter 10 and away from the puncture needle 6 is covered with a protection tube, as previously described. The end of the optical device 2 spaced from the puncture needle 6 is connected to an ocular coupling portion 36 through another bending protective connection portion 12. An illumination connection portion 38 for a light conductor of the optical device 2 is provided at the ocular coupling portion 36. By the ocular coupling portion 36, the optical device 2 is adapted to be attached to an ocular, such as a zoom ocular. The zoom ocular enables the optical device 2 to have an image with a sufficient diameter greater than 11 cm, and the outer diameter is only 0.53 mm, wherein the ripple effect can be suppressed by a suitable filter.

According to the principle of the medical device having a visual puncture apparatus according to the present invention, the puncture needle 6 and the connecter 4 can be discarded after each use, especially the puncture needle with a small diameter. Due to the very small lumen diameter, traditional methods of decontamination and complete sterilization are almost impossible. For some applications, the puncture needle 6 and the connecter 4 can also be provided as reusable and made of a material suitable for autoclaving.

In another embodiment, the visual puncture apparatus of the present application may further comprise a positioner. The positioner is arranged so that it can be detected by the above-mentioned ultrasound probe and displays relevant images on a monitor. Preferably, the positioner is a magnetic sensor and is arranged on the puncture needle. By positioning the positioner, the movement track of the puncture needle can be displayed on the monitor, so that the operator can perform the puncture operation more accurately and intuitively.

In another embodiment, the medical device having a visual puncture apparatus of the present invention can be applied to a variety of conditions and treatment methods: lithiasises, cysts, tumors, neurological diseases, facet joint diseases, spinal diseases, precision localized cell therapy, puncture guidance, biopsy, lithotripsy, cyst puncture treatment, orthopedic treatment, nerve damage treatment and targeted precision anesthesia. For example, in the lithotripsy operation of kidney lithiasises, firstly, an appropriate puncture needle is selected according to the indication and the puncture site, and the puncture point is found according to the anatomy of the puncture site. The imaging and illumination fibers of the optical device 2 may be inserted into the axial connection portion 26, the inclined connection portion 28, or another inclined connection portion 30 disposed symmetrically with the inclined connection portion 28, and enter the puncture needle 6.

The surgeon can use the shifter 10 to make the imaging and illumination fibers of the optical device 2 suitable for corresponding movement in the puncture needle 6 until the distal end of the optical device 2 is located at a suitable position in the puncture needle near the puncture tip. The locking screw 18 is then tightened to fix their relative position. The surgeon can obtain a proper field of vision through the imaging assembly and the ultrasound guiding device, and directly observe the position of the puncture needle and the condition of the tissue surrounding the puncture needle on the monitor 105. Therefore, the doctor can adjust the position of the puncture needle at any time under direct observation during the needle insertion process, avoid large blood vessels as well as major nerves and organs, and avoid accidental injury until the puncture needle approaches the lithiasis site. In addition to the optical device 2, a laser device, an irrigation tube, and the like can also be inserted through any one of the connection portions 26, 28, or 30 to perform lithotripsy treatment. Because the imaging and illumination fibers of optical devices are very thin and fragile, when using a laser for lithotripsy, especially when the fiber position is close to the lithiasis, the high laser energy is prone to damage the fiber. Therefore, a protective cover or hard fish-eye lenses made of high-quality gemstones covering on the distal end of fiber can protect optical fibers and facilitate sterilization and decontamination of optical fibers. When needed, irrigant can be infused and blood or interstitial fluid can be drawn out to obtain a clear vision and to extract lithiasis fragments, powder and the like.

Connection portions 26, 28, and 30 can also be inserted into minimally invasive surgical instruments such as biopsy forceps, micro drills, lasers, radio frequency, microwaves, sample collection devices, and energy tools such as ultrasonic lithotripsy systems and pneumatic ballistic lithotripsy systems to diagnose and treat at the same time for different operations.

Application Example I

Prostate Tumor Detection

In a famous third-class hospital in Shanghai city, when conducting medical research, the medical device of this application was used to perform an in situ examination of prostate tumors on 8 patients over 70 years old. Compared with the results of subsequent pathological examinations, the accuracy rate is more than 95%. Moreover, after the examination, the trauma is only about 2 millimeters, and the patient could take a short break and leave the hospital that day.

Application Example II

Kidney Stones Treatment

In a third-class hospital in Guangzhou city, nine patients were treated with kidney stones using the medical device of this application when conducting medical research. Because the medical device of the present application has a puncture needle, it can punch holes from the side of the body, pass through the muscle layer, and reach the intrarenal lesion directly. Then, with the help of the camera, the doctor can use a laser to break the stones under direct vision and observe whether there is any residue. The broken stones can be discharged through pipes. The time for kidney stone treatment using the medical device of this application is short, the trauma is small, the postoperative recovery period is shortened by 90%, and almost no stone remains. In contrast, with traditional kidney stone treatment, the recovery period is at least one week, and it is difficult to control the residual degree of stones, and there are often residues. In addition, when traditional kidney stones are used for treatment, there have been many cases of patients dying during the treatment of kidney stones.

Application Example III

Tumor Treatment

In a specialist tumor hospital in Shanghai, Doctor Liu, cooperated with clinical scientific research to conduct medical research on 7 male prostate tumor patients using the early prototype of this medical device. Because the medical device of the present application has a puncture needle, it can be flexibly accessed from the anal port and reach the tumor site with the shortest puncture path. Then, the doctor uses the field of vision provided by the camera to more accurately determine the trend of tumor expansion. The radiofrequency ablation device was used to ablate the tumor through the medical device, and it was observed whether there was residual tissue adjacent to the tumor. The treatment time for prostate tumors using the medical device of this application is short, the trauma is small and concealed, the postoperative recovery period is shortened to 10% of the prior period, and the tissues adjacent to the tumor are remained complete.

The medical device having a visual puncture apparatus of the present invention can be used as an endoscope, which has the following advantages:

I. During the preoperative puncture, the medical device perform puncturing with a camera, especially in combination with ultrasound navigation. Combined the advantages of the overall observation of the overall general site and the surrounding environment by ultrasound positioning with the advantages of the detailed observation of the microenvironment surrounding the needle tip by the puncture needle, the details of the puncture process are intuitively reflected on the monitor like a camera, and the puncture can reach the lesion directly. The whole process of the puncture process is visible to avoid mis-puncture, which is different from the ultrasound or radiology indirect image localization puncture. The puncture process is intuitive and real-time. The medical device uses a puncture needle as small as 4.0 Fr, and directly reaches the lesion through the puncture, and can perform various laser, radio frequency, microwave and other instruments for interventional treatment through the interior of the puncture needle. After the one-step puncture, the 4.0 Fr puncture needle does not need to be replaced with a reaming cannula for expansion, and directly enters the treatment mode.

II. During the surgical treatment process, the entire interventional treatment process is still under the real-time monitoring of the system. The scope, extent, effect and length of the appropriate treatment time can be reflected on the monitor in real time through the system, thereby obtaining an intuitive assessment and greatly improving the safety of interventional surgery. And because its process is safe and visible, the conventional microwave, radio frequency and other conventional energy tools have been expanded, more accurate and safe treatment tools such as lasers have been added, and surgery can be performed under direct vision, where contrast media can be injected or the drug can be administrated directly at the lesion. The risky treatment method was liberated due to the intuitiveness brought by visual puncture, which improved the accuracy and safety of the conventional interventional surgery and expanded the scope of indications. This technology that greatly improves accuracy and safety is especially important for the elderly. Various calcifications, cysts, and degenerative diseases are common for the elderly people, and major surgery is not recommended if it is not necessary. Therefore, a safe positioning and precisely treated interventional surgery is one of the least expensive surgical methods for the elderly people.

III. The postoperative evaluation is intuitive, the operation is repeatable, and the postoperative recovery time is short. Because the wound area caused by the device can be as small as 1.9 square millimeters, compared with tens to hundreds of square millimeters in conventional minimally invasive surgery, it has the characteristics of small trauma, intuitiveness and repeatability, so it can also be positioned intuitively and accurately to the original surgical treatment point for postoperative evaluation and accurate correction treatment. For cases in need, you can still "retrieve" the original treatment point in nearly non-invasive way for a visual observation within a period of time after the operation, and if necessary, even further precise correction treatments can be carried out, all this in the past is impossible to achieve.

IV. It has a wide range of applications and can be used for the following treatments: 1. Percutaneous nephrolithotomy; 2. Kidney Stones at sites with IPA angles ≤30° or stones ≤2 cm in the inferior renal calyx; 3. Visually and safely establish puncture channels to ensure all intervention therapy can be performed safely; 4. Puncture of renal cysts; 5. Puncture guidance of nephrostomy; 6. Cystoscopy/bladder stone treatment; 7. Examination and treatment of seminal vesicles and scrotum; 8. Pediatric kidney stones treatment; 9. Fetal giant bladder disease (congenital ureteral cyst); 10. Renal calyx diverticulum stones; 12. Fetal microscopy, combined with other means to treat congenital diseases, etc.

Aspects of the embodiments can be modified, if necessary, to employ aspects, features, and concepts of the various patents, applications, and publications to provide additional embodiments.

In view of the above detailed description, these and other changes can be made to the embodiments. In general, the terms used in the claims should not be considered limited to the specific embodiments disclosed in the description and the claims, but should be understood to comprise all possible embodiments together with all equivalents enjoyed by these claims range.

The invention claimed is:

1. A medical device having a visual puncture apparatus, wherein the visual puncture apparatus comprises a puncture assembly, an imaging assembly, and a display device, wherein the puncture assembly comprises a puncture needle and a puncture cannula, wherein the puncture cannula is detachably sleeved around the puncture needle, the distal end of the puncture needle has a puncture tip that protrudes from the puncture cannula, the puncture assembly has a working channel provided in the puncture cannula, the imaging assembly is configured to enable image acquiring, transmitting and processing, at least a part of the imaging assembly is arranged in the working channel, and the display device is used to display an image from the imaging assembly, wherein the working channel is configured for simultaneously arranging at least a part of the imaging assembly and additional instruments in the working channel, wherein the instruments are one or more selected from the following: a laser, a radio frequency device, a microwave device, an ultrasonic lithotripsy system, a pneumatic ballistic lithotripsy system, a vibration device, a radiofrequency ablation device, and a sample collecting device;

an outer diameter of the puncture needle or the puncture cannula is 0.35 mm to 3.2 mm;

the visual puncture apparatus further comprises a multi-ports connector, wherein the multi-ports connector is disposed at a proximal end of the puncture assembly and is operably connected with the puncture cannula; the multi-port connector has several ports, wherein at least one of the ports receives the additional instruments for entering or quitting the puncture cannula through the at least one of the ports, and at least another port receives the at least a part of the imaging assembly for entering or quitting through the at least another port;

the multi-ports connector further comprising a puncture needle connection portion such that the puncture needle is releasably connectable to the multi-ports connector, wherein the multi-ports connector is configured such that the puncture needle and the imaging assembly are further connected to the multi-ports connector such that the imaging assembly is inserted into the multi-ports connector and then into the puncture needle so that a whole process of the puncture is visible, and wherein the multi-ports connector is configured such that the puncture needle and the imaging assembly are separable from the puncture cannula after puncturing is completed, and such that after the puncture needle is separated from the puncture cannula, a part of the imaging assembly is inserted into the working channel through one of the ports of the multi-ports connector, and the additional instrument is inserted into the working channel through another port simultaneously.

2. The medical device according to claim 1, wherein the working channel is a single channel without any internal partition.

3. The medical device according to claim 1, wherein the puncture needle is detachably connected to the imaging assembly.

4. The medical device according to claim 1, wherein the visual puncture apparatus further comprises a light source, and the imaging assembly of the medical device comprises imaging and illumination fibers, wherein the imaging and illumination fibers extend through the puncture needle or the puncture cannula and is connected to the light source.

5. The medical device according to claim 4, wherein the visual puncture apparatus further comprises a shifter configured to adjust a relative position between the imaging and illumination fibers and the puncture needle or the puncture cannula.

6. The medical device according to claim 4, wherein a lens assembly is provided at distal ends of the imaging and illumination fibers.

7. The medical device according to claim 4, wherein distal ends of the imaging and illumination fibers are provided with a lens made of a gemstone having a Mohs hardness higher than 7.5.

8. The medical device according to claim 1, wherein the imaging assembly further comprises a lens assembly, the lens assembly being located inside a distal end of the puncture needle when the imaging assembly is inserted into the puncture needle;

alternatively, the imaging assembly comprises a signal transmitting cable and an image sensor, wherein the image sensor is disposed at the distal end of the puncture needle or puncture cannula when inserted into the puncture needle or the puncture cannula, and is electrically connected to the display device via the signal transmitting cable extending through the puncture needle or the interior of the puncture cannula.

9. The medical device according to claim 1, wherein the medical device is suitable for the following diseases: lithiasises, cysts, tumors, neurological diseases, facet joint diseases, spinal diseases, precision localized cell therapy, orthopedic treatments, nerve damage treatment and targeted anesthesia.

10. The medical device according to claim 1, wherein the visual puncture apparatus further comprises an ultrasound probe, and the display device is further configured to display images from the ultrasound probe.

11. The medical device according to claim 10, wherein the visual puncture apparatus further comprises a positioner arranged such that it is capable of being detected by the ultrasound probe and images of the positioner are shown on the display device.

12. The medical device according to claim 11, wherein the positioner is a magnetic sensor.

* * * * *